US010657425B2

(12) United States Patent
Martinello et al.

(10) Patent No.: US 10,657,425 B2
(45) Date of Patent: May 19, 2020

(54) DEEP LEARNING ARCHITECTURES FOR THE CLASSIFICATION OF OBJECTS CAPTURED WITH A LIGHT-FIELD CAMERA

(71) Applicants: Manuel Martinello, Mountain View, CA (US); Leonidas Spinoulas, San Jose, CA (US)

(72) Inventors: Manuel Martinello, Mountain View, CA (US); Leonidas Spinoulas, San Jose, CA (US)

(73) Assignee: Ricoh Company, Ltd., Tokyo (JP)

(*) Notice: Subject to any disclaimer, the term of this patent is extended or adjusted under 35 U.S.C. 154(b) by 44 days.

(21) Appl. No.: 15/917,473

(22) Filed: Mar. 9, 2018

(65) Prior Publication Data
US 2019/0279051 A1    Sep. 12, 2019

(51) Int. Cl.
*G06K 9/66* (2006.01)
*G06K 9/32* (2006.01)
(Continued)

(52) U.S. Cl.
CPC ............ *G06K 9/66* (2013.01); *A61B 1/227* (2013.01); *A61B 3/0058* (2013.01);
(Continued)

(58) Field of Classification Search
CPC ...... G06K 9/66; G06K 9/3233; G06K 9/6268; G06K 2209/05; G06K 9/6232;
(Continued)

(56) References Cited

U.S. PATENT DOCUMENTS

2015/0035803 A1    2/2015   Wassvik et al.
2015/0065803 A1*   3/2015   Douglas ............. A61B 1/00009
                                                      600/200
(Continued)

FOREIGN PATENT DOCUMENTS

CN    107392234 A    11/2017
JP    2014-049118 A   3/2014
JP    2017-146957 A   8/2017

OTHER PUBLICATIONS

Wu et al. "Light Field Image Processing: An Overview." IEEE Journal of Selected Topics in Signal Processing, vol. 11, No. 7, Oct. 2017, pp. 926-954 (Year: 2017).*
(Continued)

*Primary Examiner* — Jon Chang
(74) *Attorney, Agent, or Firm* — Fenwick & West LLP

(57) ABSTRACT

Light-field data is masked to identify regions of interest, before applying to deep learning models. In one approach, a light-field camera captures a light-field image of an object to be classified. The light-field image includes a plurality of views of the object taken simultaneously from different viewpoints. The light-field image is pre-processed, with the resulting data provided as input to a deep learning model. The pre-processing includes determining and then applying masks to select regions of interest within the light-field data. In this way, less relevant data can be excluded from the deep learning model. Based on the masked data, the deep learning model produces a decision classifying the object.

17 Claims, 11 Drawing Sheets
(7 of 11 Drawing Sheet(s) Filed in Color)

(51) Int. Cl.
  *G06K 9/62*   (2006.01)
  *A61B 1/227*  (2006.01)
  *G06T 7/557*  (2017.01)
  *G06N 5/02*   (2006.01)
  *A61B 3/00*   (2006.01)

(52) U.S. Cl.
  CPC ......... *G06K 9/3233* (2013.01); *G06K 9/6232* (2013.01); *G06K 9/6268* (2013.01); *G06K 9/6271* (2013.01); *G06N 5/02* (2013.01); *G06T 7/557* (2017.01); *G06K 2209/05* (2013.01)

(58) Field of Classification Search
  CPC ........ G06K 9/6271; G06T 7/557; G06N 5/02; G06N 20/00; A61B 3/0058; A61B 1/227
  See application file for complete search history.

(56) References Cited

U.S. PATENT DOCUMENTS

2016/0180195 A1* 6/2016 Martinson ............ G06K 9/6256
                                                   382/103
2017/0200067 A1   7/2017 Zhou et al.
2017/0256059 A1   9/2017 Tosic et al.

OTHER PUBLICATIONS

Raghavendra et al. "Combining Iris and Periocular Recognition using Light Field Camera." 2nd IAPR Asian Conference on Pattern Recognition, Nov. 5, 2013, pp. 155-159 (Year: 2013).*

Wang, T. et al., "A 4D Light-Field Dataset and CNN Architectures for Material Recognition," European Conference on Computer Vision, 2016, 16 pages.

European Patent Office, Extended European Search Report and Opinion, EP Patent Application No. 19160959.3, Jul. 24, 2019, ten pages.

Zhu, H. et al., "Light field imaging: models, calibrations, reconstructions, and applications," Frontiers of Information Technology & Electronic Engineering, vol. 18, No. 9, Oct. 27, 2017, pp. 1236-1249.

Japanese Patent Office, Notice of Reasons for Refusal, JP Patent Application No. 2019-026989, dated Feb. 12, 2020, 14 pages.

* cited by examiner

DEEP LEARNING ARCHITECTURES FOR THE CLASSIFICATION OF OBJECTS CAPTURED WITH A LIGHT-FIELD CAMERA

BACKGROUND

1. Technical Field

This disclosure relates generally to light-field images, and more particularly, to processing light-field images using deep learning models.

2. Description of Related Art

The light-field camera has recently received increased attention. It can be used to recalculate a different focus point or point of view of an object, based on digital processing of the captured light-field image. The light-field camera also finds application in estimating depth to three-dimensional objects that are imaged by the light-field camera, possibly followed by three-dimensional reconstruction of those objects or the entire three-dimensional scene.

In addition, deep learning has also recently received increased attention. Much research has been directed to studying a multitude of deep learning architectures for solving a variety of classification problems. For image processing applications, typically, a training set of images is used to train the deep learning model and, once trained, the model can be used to classify new images. However, selection of the training set and pre-processing of the images can be an important aspect affecting the performance of the model. Furthermore, light-field images contain information that is different from the information in conventional two-dimensional images. However, to date, there has not been much research on how to architect deep learning models to work with light-field images.

Thus, there is a need for better approaches to combine deep learning with light-field images.

SUMMARY

The present disclosure overcomes the limitations of the prior art by masking light-field data to identify regions of interest, before applying to deep learning models. In one approach, a light-field camera captures a light-field image of an object to be classified. The light-field image includes many views of the object taken simultaneously from different viewpoints. The light-field image is pre-processed, with the resulting data provided as input to a deep learning model. The pre-processing includes determining and then applying masks to select regions of interest within the light-field data. In this way, less relevant data can be excluded from the deep learning model. Based on the masked data, the deep learning model produces a decision classifying the object.

The masking can be determined in different ways, for example based on depth information extracted from the light-field image or based on the pixel values within the light-field image. The masking can also be applied at different stages: to the entire light-field image at once, applied separately to each of the views, applied separately for different color channels, or applied to epipolar images generated from the light-field image, just to give a few examples.

Other aspects include components, devices, systems, improvements, methods, processes, applications, computer readable mediums, and other technologies related to any of the above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
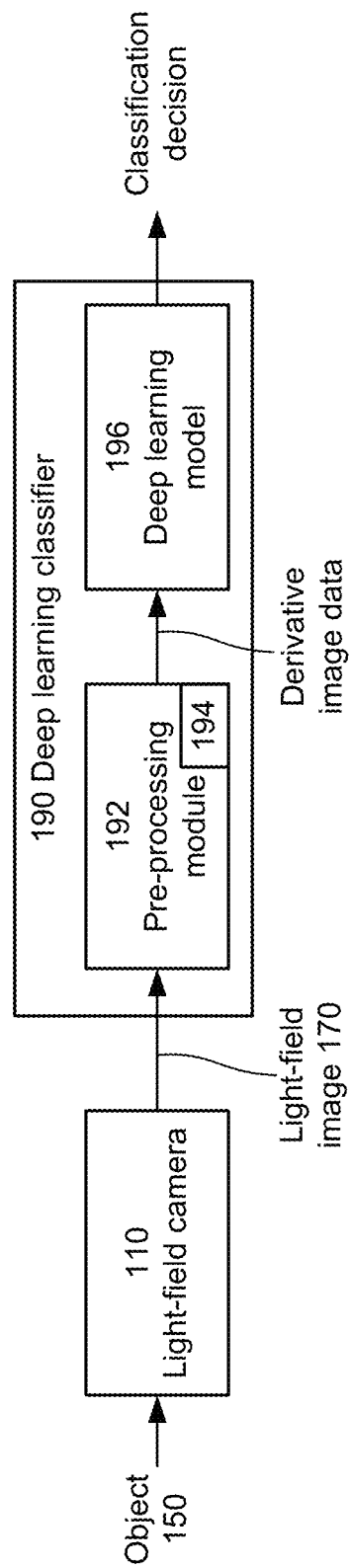
FIG. 1 is a block diagram of a system according to an embodiment.

FIG. 1 is a block diagram of a system according to an embodiment. The system is used to classify an object. As an example, in one application, the object is a patient's eardrum and the system classifies a condition of the ear drum. Factors such as color, translucency and shape (bulging, normal or retracting) can be used to classify the eardrum condition as acute otitis media (AOM), otitis media with effusion (OME), or otitis media with no effusion (NOE), as described in Table 1 below. This is just one example. Other applications will be apparent.

TABLE 1

| Otoscopic findings associated with clinical diagnostic categories on TM images | | | |
|---|---|---|---|
|  | AOM | OME | NOE |
| Color | White, pale yellow, markedly red | White, amber, gray, blue | Gray, pink |
| Shape | Distinctly full, bulging | Neutral, retracted | Neutral, retracted |
| Translucency | Opacified | Opacified, semi-opacified | Translucent |

The system includes a light-field camera 110 and a deep-learning classifier 190. The classifier 190 in turn includes a pre-processing module 192 and a deep learning model 196. The deep-learning classifier 190 is typically implemented as a computer system with processor and computer instructions. The light-field camera 110 captures light-field images 170 of objects 150. Each light-field image 170 contains many views of the object 150 taken simultaneously from different viewpoints.

The pre-processing module 192 receives the light-field images from the camera. It may do so through a standardized interface (not shown in FIG. 1). The pre-processing module 192 pre-processes the light-field image to ready the data for the deep learning model 196. Pre-processing may include various functions, such as scaling, normalization, image registration, etc. In this example, the pre-processing includes a masking function 194 to select the regions of interest within the light-field data. The module 192 determines the masking and applies it to the light-field data. The result of the pre-processing, which will be referred to as derivative image data, is input to the deep learning model 196, which produces a decision classifying the object.

Figure 2A:
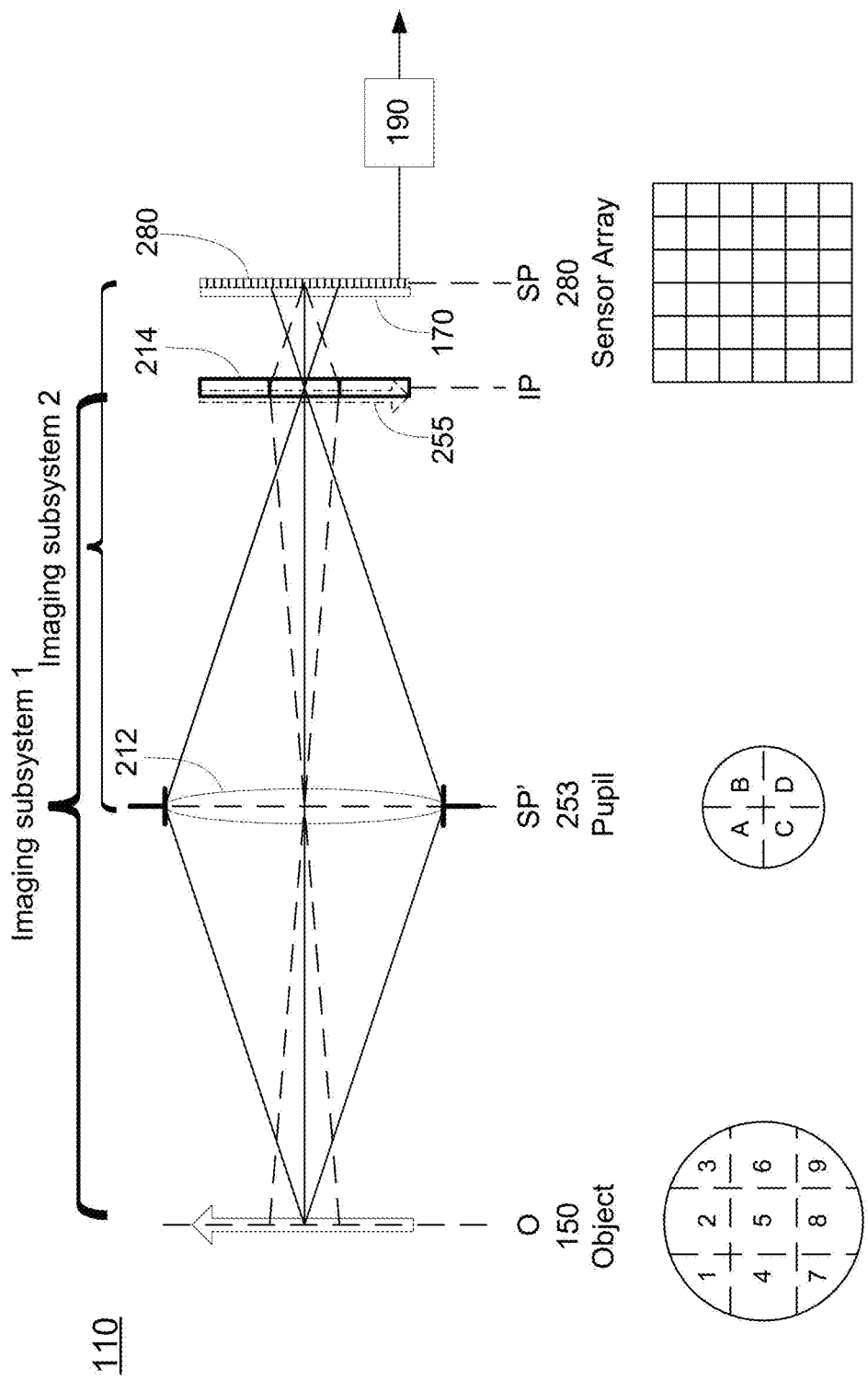
FIGS. 2A-2B are diagrams illustrating a light-field camera, according to an embodiment.
Figure 2B:
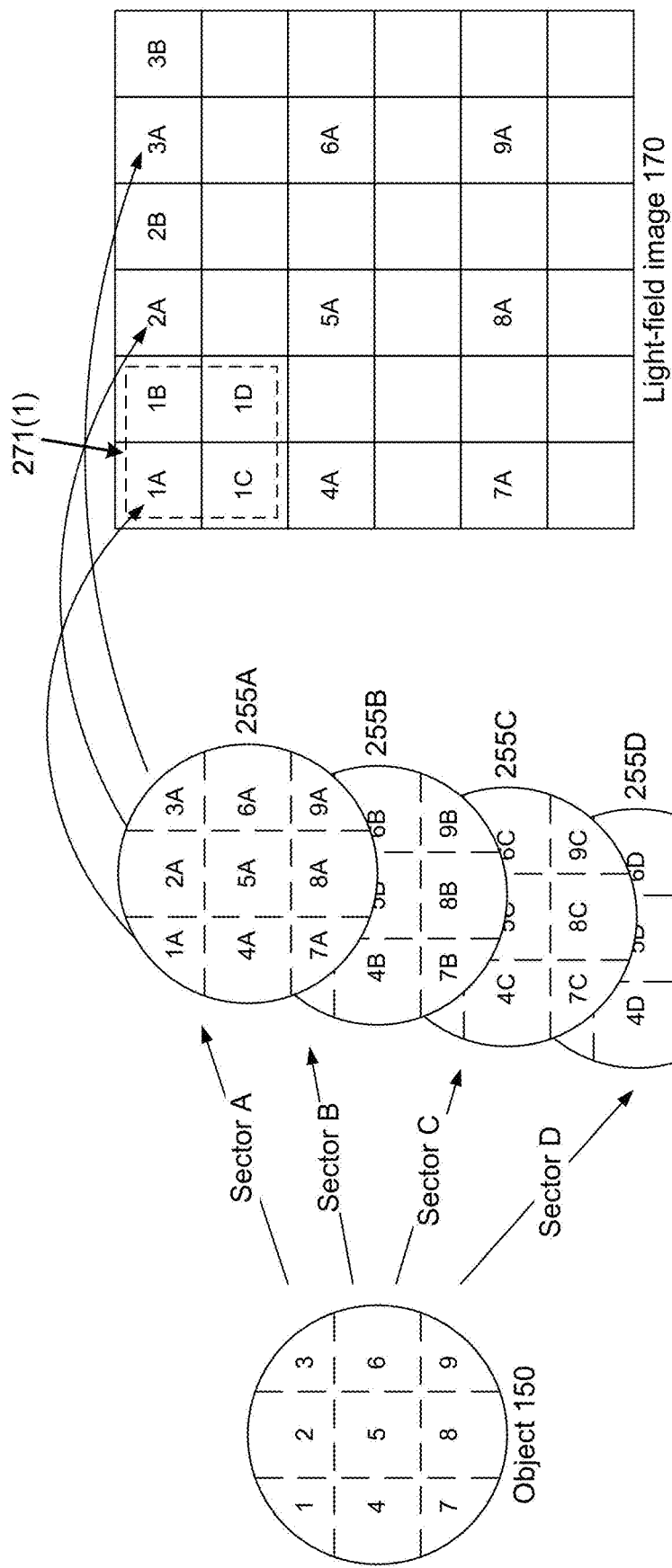

Now consider each of the components shown in FIG. 1. FIGS. 2A-2B are diagrams illustrating an example of a light-field camera 110. The camera 110 includes an objective lens 212 (represented by a single lens in FIG. 2A), a secondary imaging array 214 (an array of image forming elements) and a sensor array 280. For convenience, the imaging optics 212 is depicted in FIG. 2A as a single optical element, but it should be understood that it could contain multiple elements.

The secondary imaging array 214 may be referred to as a microimaging array. The secondary imaging array 214 and sensor array 280 together may be referred to as a light-field sensor module. In this example, the secondary imaging array 214 is a microlens array. Other examples of microimaging arrays 214 include arrays of pinholes and waveguide/channel arrays. The microimaging array 214 can be a rectangular array, hexagonal array or other types of arrays.

These components form two overlapping imaging subsystems. In the first imaging subsystem, the objective lens 212 forms an optical image 255 of the object 150 at the primary image plane IP. This imaging subsystem has a pupil plane, marked SP' in FIG. 2A. In the second imaging subsystem, the secondary imaging array 214 images the pupil plane SP' onto the sensor array 280. To do this, the microimaging array 214 is located at the image plane IP or one of its conjugate planes. The system in its entirety forms a light-field image 170 of the object at the sensor plane SP. The object 150 and image plane IP form one set of conjugate surfaces. The pupil 253 and sensor plane SP form another set of conjugate surfaces.

The bottom portion of FIG. 2A provides more detail. In this diagram, the object 150 is divided into 3×3 areas 1-9, and the pupil 253 is divided into 2×2 sectors A-D (sometimes referred to as sub-apertures A-D). The sensor array 280 is shown as a 6×6 rectangular array.

FIG. 2B illustrates conceptually how the light-field image 170 is produced. Light rays leave the object 150, pass through the pupil 253 and form an image 255 at the primary image plane IP. That image 255 can be divided into component images 255A-D as follows. Some of the light rays from the object travel through sub-aperture A of the pupil, and some travel through sub-apertures B, C or D, respectively. The rays that travel through sub-aperture A would produce an optical image 255A, which is just one component in the actual image 255. For convenience, the 3×3 areas in component image 255A are labeled with the suffix A: 1A-9A. The image 255A is sometimes referred to as the view of the object 150 taken from the viewpoint A. Similarly, the rays that travel through sub-apertures B, C, D would produce corresponding optical images 255B, C, D with 3×3 areas labeled 1B-9B, 1C-9C and 1D-9D. These images 255B, C, D are additional views of the object 150, taken from different viewpoints B, C, D. In FIG. 2A, the aerial image 255 is the combination of all of the views 255A-D. A sensor array positioned at the image plane IP would capture an image with contributions from all of the views.

However, the different views 255A-D are separated in an interleaved fashion at the sensor plane, as shown in FIG. 2B. Using image 255A as an example, the 3×3 areas 1A-9A from optical image 255A are not contiguous in a 3×3 block within the light-field image 170. Rather, areas 1A, 1B, 1C and 1D, from the four different views, are arranged in a 2×2 fashion in the upper left of the light-field image 170 (the inversion of image 170 is neglected for clarity).

Areas 1-9 are similarly arranged. Thus, the areas 1A-9A that make up view 170A are spread out across the composite light-field image 170, separated by portions of the other views 170B-D. Put in another way, if the sensor is a rectangular array of individual sensor elements, the overall array can be divided into rectangular subarrays 271(1)-(9) of sensor elements (only one subarray 271(1) is shown by the dashed lines in FIG. 2B). For each area 1-9 of the object, all of the corresponding areas from each view are imaged onto the subarray. For example, areas 1A, 1B, 1C and 1D are all imaged onto subarray 271(1). Note that since the pupil 253 and sensor array 280 are located in conjugate planes, each imaging element in array 214 forms an image of the pupil 253 at the sensor plane SP. Since there are multiple imaging elements, multiple images 271 of the pupil 253 are formed.

It should be noted that FIG. 2 has been simplified to illustrate underlying concepts. For example, the object 150 was artificially divided into an array in order to more easily explain the overall light-field imaging function. As another example, most practical systems will use significantly larger arrays, particularly at the sensor array. In addition, there need not be a 2:1 relationship between the 6×6 regions at the sensor plane and the underlying sensor elements in the sensor array. Each region could correspond to multiple sensor elements, for example. As a final example, the areas labeled 1 in the object, 1A in the view 255A and 1A in the light-field image 170 do not have to be exact images of each other. In some designs, area 1A within image 170 may capture the energy approximately from area 1 in the object 150, but it may not actually be an image of area 1. Thus, the energy collected by sensor elements in area 1A of image 170 may be integrating and sampling the image (or some transformation of the image) in area 1 of the object 150, rather than representing a geometrical reproduction of the object at that area. In addition, effects such as parallax, vignetting, diffraction and optical propagation may affect any image formation.

The light-field image 170 is processed by the deep-learning classifier 190. FIGS. 3 and 4 show examples of masking in the pre-processing module of the deep-learning classifier. In these examples, the light-field images are images of the ear interior captured by a light-field otoscope. The light-field otoscope has a 320×260 array of microlenses, with 11×11 pixels under each microlens. Thus, the light-field image includes 11×11=121 views of the ear interior taken from different viewpoints. We eliminate the boundary viewpoints where the viewing angles are very oblique and consider only 7×7=49 views.

Figure 3B:
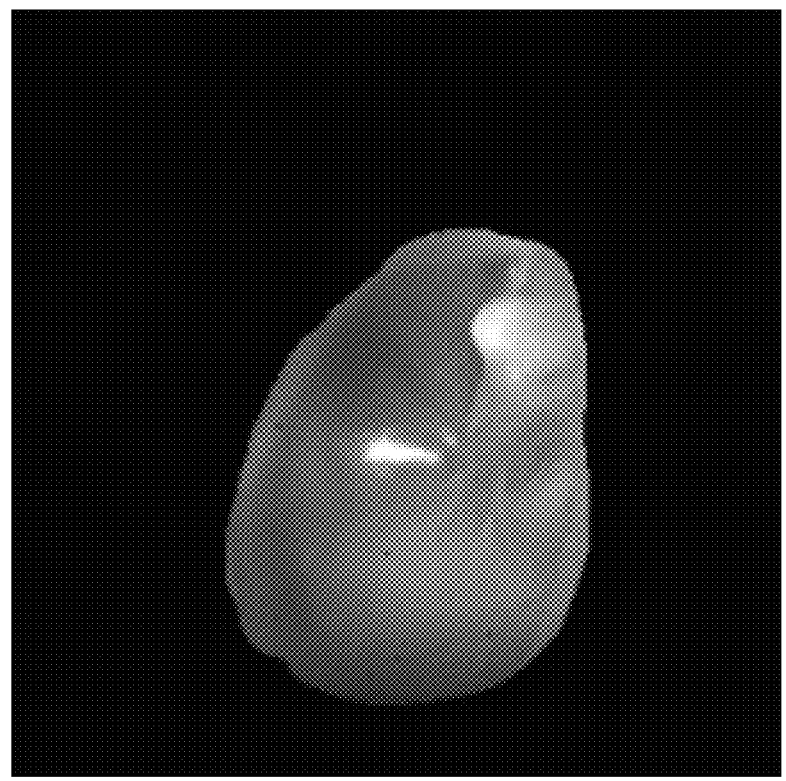
FIGS. 3A and 3B show a central view captured by a light-field camera, before and after masking, respectively, according to an embodiment.
Figure 3A:
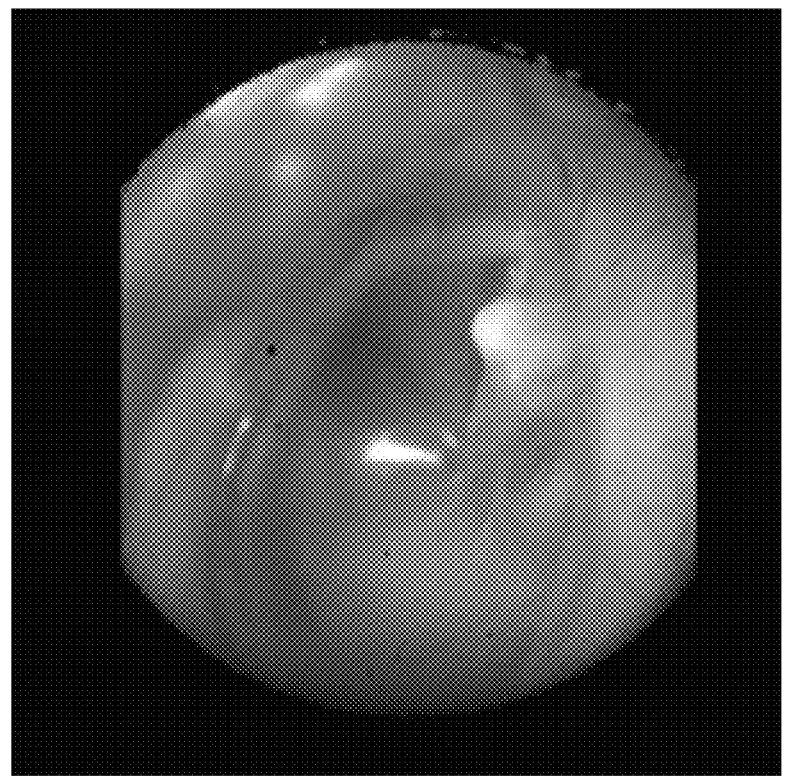

FIG. 3A shows the center view captured by the otoscope. The goal is to classify the condition of the eardrum, so the portion of the image showing the ear canal outside the eardrum is less relevant. FIG. 3B shows the same view, but with a mask applied to select just the region of interest. With eardrums, we have obtained meaningful results only when we have been able to mask the ear canal and the dark area around the image, leaving primarily only the eardrum. Proper masking forces the deep learning model to classify based only on the region of interest. During training, it allows the deep learning model to train just on the region of interest, so that details or common patterns in the background do not interfere in the learning process. The mask does not have to be exactly correct. For example, a slightly larger mask that allowed some of the background to remain also worked well.

Figure 4B:
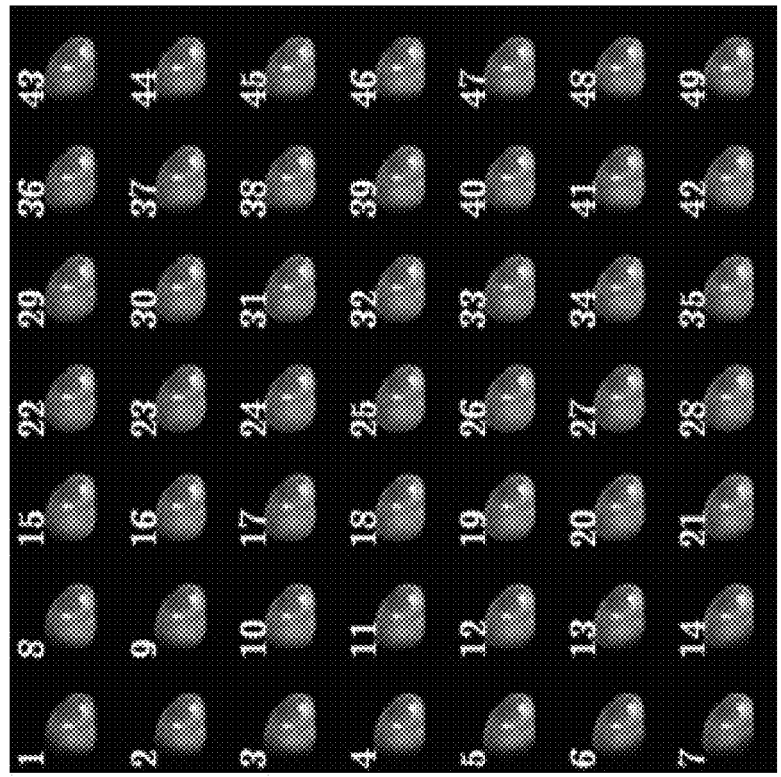
FIGS. 4A and 4B show 7×7 arrays of views captured by a light-field camera, before and after masking, respectively, according to an embodiment.
Figure 4A:
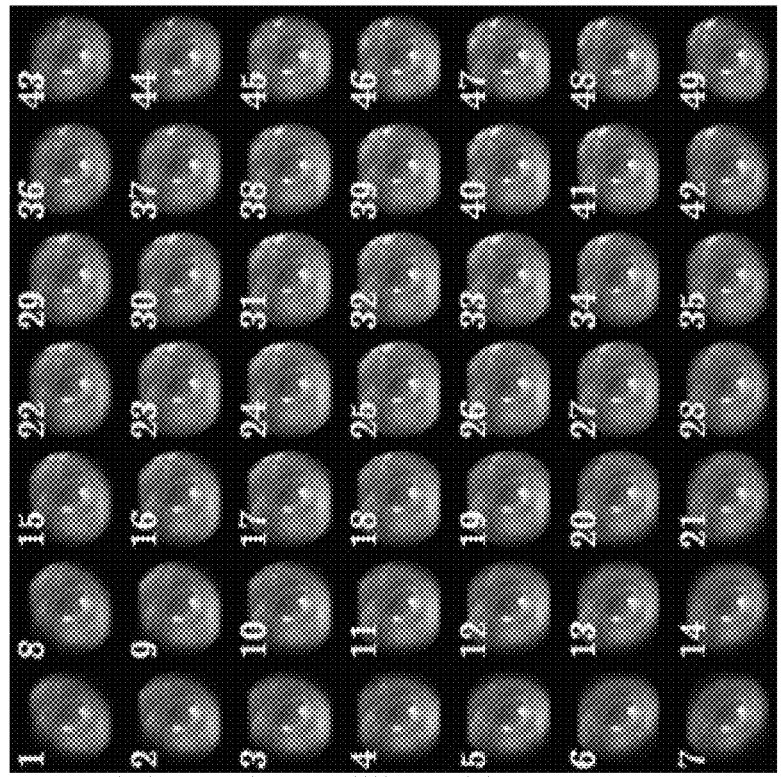

FIG. 4A shows all 49 views and FIG. 4B shows all 49 views after masking. Note that FIG. 4A is not the raw light-field image captured by the light-field camera. The raw light-field image contains this data, but the different views are interleaved in the light-field image as described in FIG. 2B.

Figure 5C:
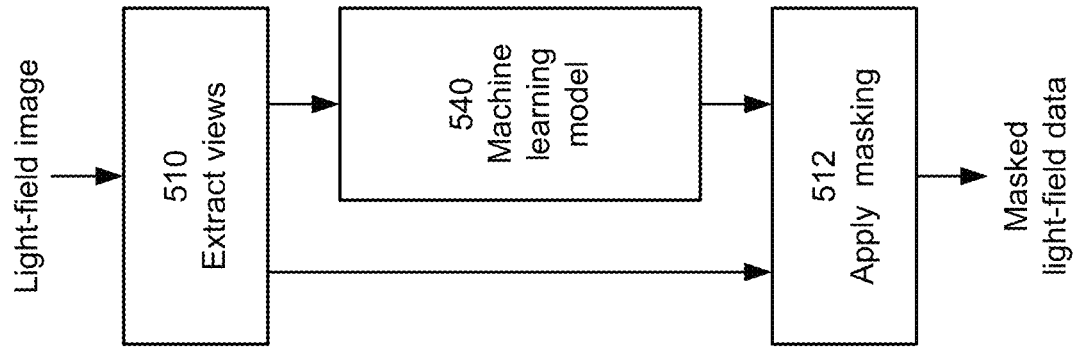
FIGS. 5A-5C are flow diagrams illustrating different methods for generating masking, according to various embodiments.
Figure 5B:
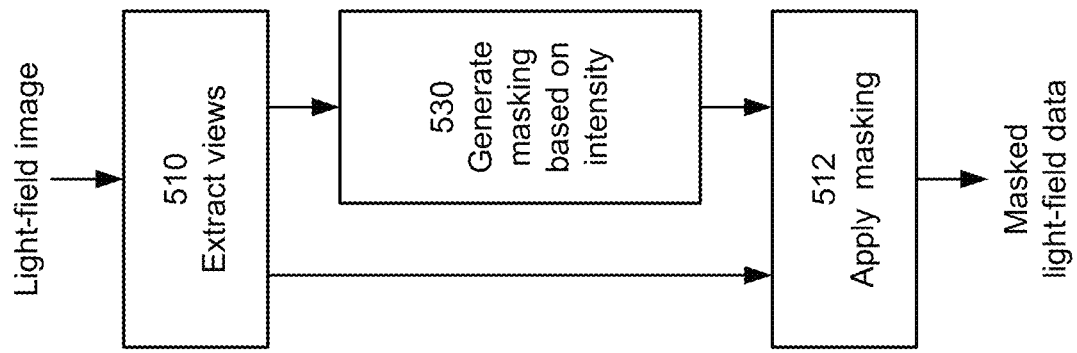
Figure 5A:
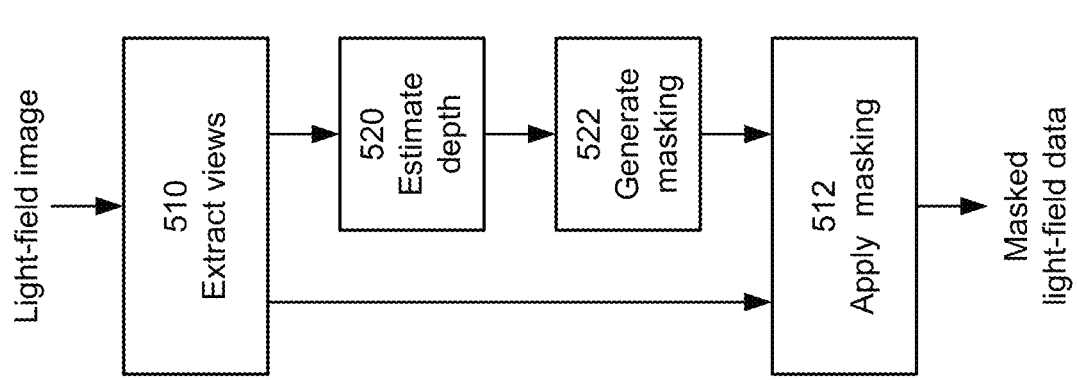

Masking can be determined using different techniques, some examples of which are shown in FIGS. 5A-5C. In FIG. 5A, the masking is based on depth information. The individual views are extracted 510 from the light-field image. The views are images of the object taken from different viewpoints. The parallax between views can be used to estimate 520 depth to the object. Masking is then generated 522 based on the depth information, for example by thresholding the depth. In the ear example, the depth information provides information about the eardrum location compared to the sides of the ear canal. This can be used to form masks to isolate the eardrum. The masks are applied 512 to the views to produce inputs to the deep learning model.

In FIG. 5B, the masking is based on image content. In this example, it is based on intensity values. For example, the region of interest may be brighter than the background, so that the masking can be generated by thresholding the intensity 530 of pixels in the images. Other examples include masking based on color, or based on identification of certain objects, for example. In FIG. 5C, a machine learning model 540 is trained to determine masking for the light-field data.

Masking can also be manually generated, for example by having a person outline the region of interest. Alternately, it can be automatically generated, for example by segmenting the views into different regions based on identified features. In yet another approach, masking may be generated by comparing a current image with a previous image and selecting only the differences.

In another aspect, the masks may be binary, taking on values of 1 or 0, as in the examples of FIGS. 3 and 4. However, they may also be continuous, taking on values in the range [0,1]. This is a grayscale mask. For example, masking produced by a machine learning model may take continuous values reflecting the confidence whether a certain pixel should be masked or not.

The masks can also be applied to different types of light-field data. In FIGS. 5A-5C, masking is generated for different views and then applied to each view. In a case such as FIG. 3 where only one view is used and the classification decision is made based only on that one view, then the masking may be applied to only that one view. In cases such as FIG. 4 where many views are used to make the classification decision, masking may be separately generated and applied to each of the views, or the same masking may be applied to all views, or views may be grouped together or combined together with masking generated for each group. This last approach may be advantageous if views are similar.

Various other combinations are possible. FIGS. 6-10 provide some examples of different types of masking used with different deep learning architectures. In these examples, the light-field image contains $h_a \times w_a = m$ views, each view is $h_s \times w_s$ pixels with red, green and blue color channels. Here, the subscript "a" is for "angle," and the subscript "s" is for "space."

Figure 6:
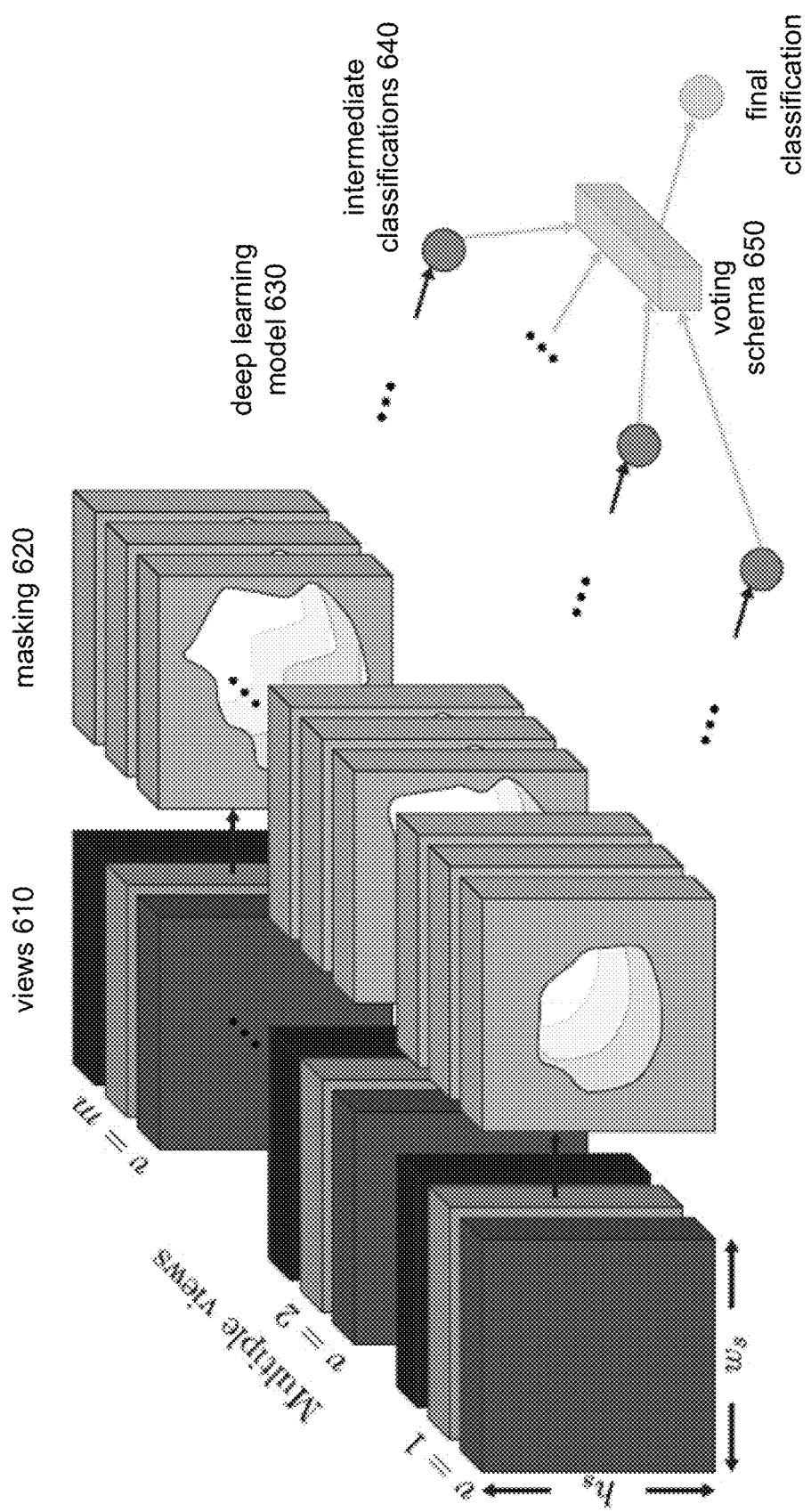
FIGS. 6-10 are diagrams illustrating masking for different deep learning architectures, according to various embodiments.

In FIG. 6, the lefthand side shows the m views 610, with three color channels for each view. The masking 620 is one set of masks for each view. The masks for different views may be different and will depend on the content of that view. For each view, the same mask is applied to each of the R,G,B color components. The deep learning model 630 has separate decision networks for each view. Each masked view is input to its corresponding decision network of the deep learning model 630, which produces an intermediate decision 640 for that view. For m views, there are m intermediate classification decisions 640. These are combined by a voting schema 650 to produce the final classification.

Different types of voting schema can be used. Majority voting, plurality voting and weighted voting are some examples. In weighted majority voting, the majority vote wins but the intermediate decisions are given unequal weights. In one approach, the weighting is related to the masking used to produce that intermediate decision. In addition, the voting schema does not have to output a binary decision (as with majority voting). Rather, the intermediate decisions can be combined to produce a continuous final decision (e.g., probability of outcome). The voting schema may also be machine-based and learned.

Different deep learning architectures will be apparent. Deep learning architectures include multiple layers. Each layer typically includes a set of filters applied to a set of inputs (images or views in this case), and a non-linear step (e.g., a voting schema) which reduces the size of the output. When the filtering is a convolution between the inputs and the filters, the architecture is typically referred to as a convolutional neural network (CNN). When the network has only a few layers, it is a shallow network. When the number of layers is high, it is a deep learning network. Because of the multiple layers, a deep learning network is computationally and spatially expensive to implement. Masking the input image or the first layers drastically reduces the overall complexity of the network.

Figure 7:
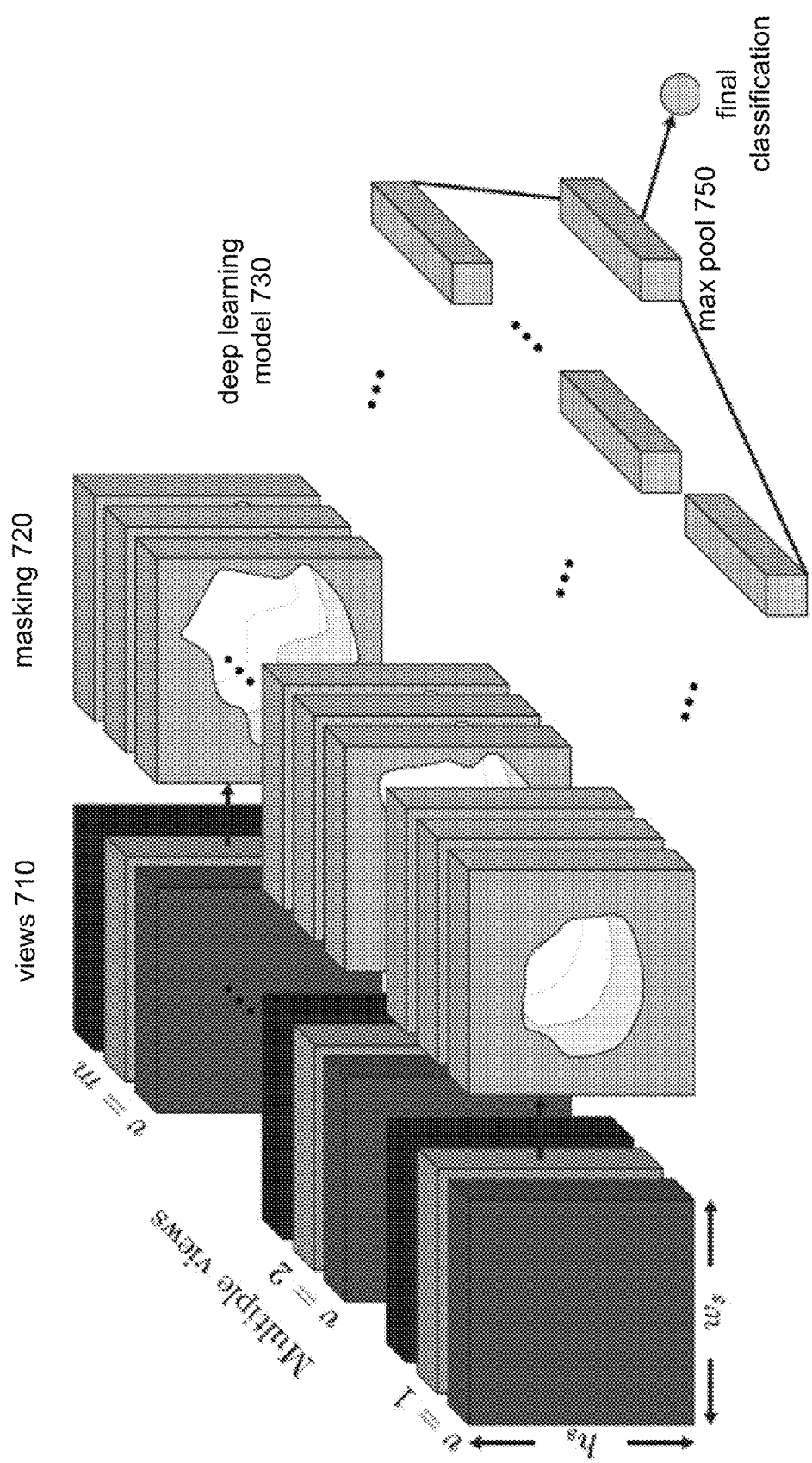

In FIG. 7, the masking 720 is one set of masks for each view 710, as in FIG. 6. However, the deep learning model 730 has a different architecture. It does not produce one intermediate decision for each view. Rather, each masked view is passed through the convolutional part of the network separately. Then, they are aggregated at a max view-pooling layer 750, and then sent through the remaining (fully-connected) part of the network. This method combines information from different views at a higher level. However, max pooling selects only one input, so still only one view is chosen at each pixel.

FIG. 7 illustrates a reduction of the light-field data with respect to the (view) dimension. Other types of reductions are also possible. The light-field data can be modeled as a four-dimensional data set $L^i(x,y,u,v)$, where L is the intensity value of a pixel, (x,y) are the two (image) dimensions, and (u,v) are the two (view) dimensions. The superscript i is an index for the channel, which in this example is a color channel. Reduction can be made along any of these dimensions. The (view) dimension may be reduced, as in FIG. 7, by combining or grouping different views in the pre-processing or in the deep learning model. The (image) dimension may be reduced by considering different scales for the images. In one approach, a pyramid of successively downsampled images is used to address effects at different scales. The (channel) dimension may be similarly reduced.

Figure 8:
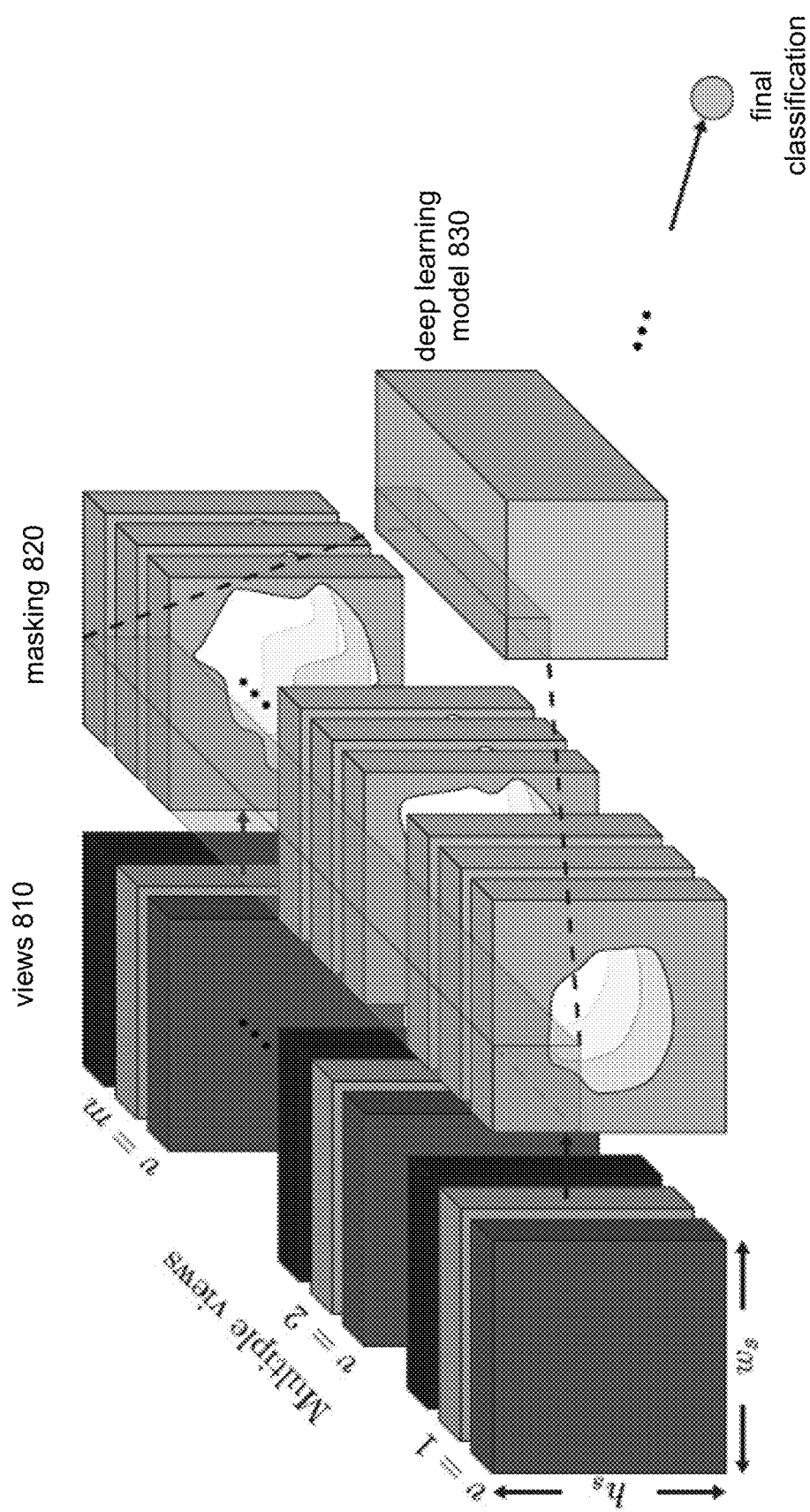

For example, in FIG. 8, all of the different views 810 are stacked across their RGB channels and the corresponding masks 820 are applied before feeding them into the network 830. This has the advantage that all views are combined earlier, thus consuming far less memory. As illustrated, the masking preferably is applied before reduction because that leads to the greatest reduction in complexity. It can also be applied after reduction but with less reduction of the overall complexity.

Figure 9:
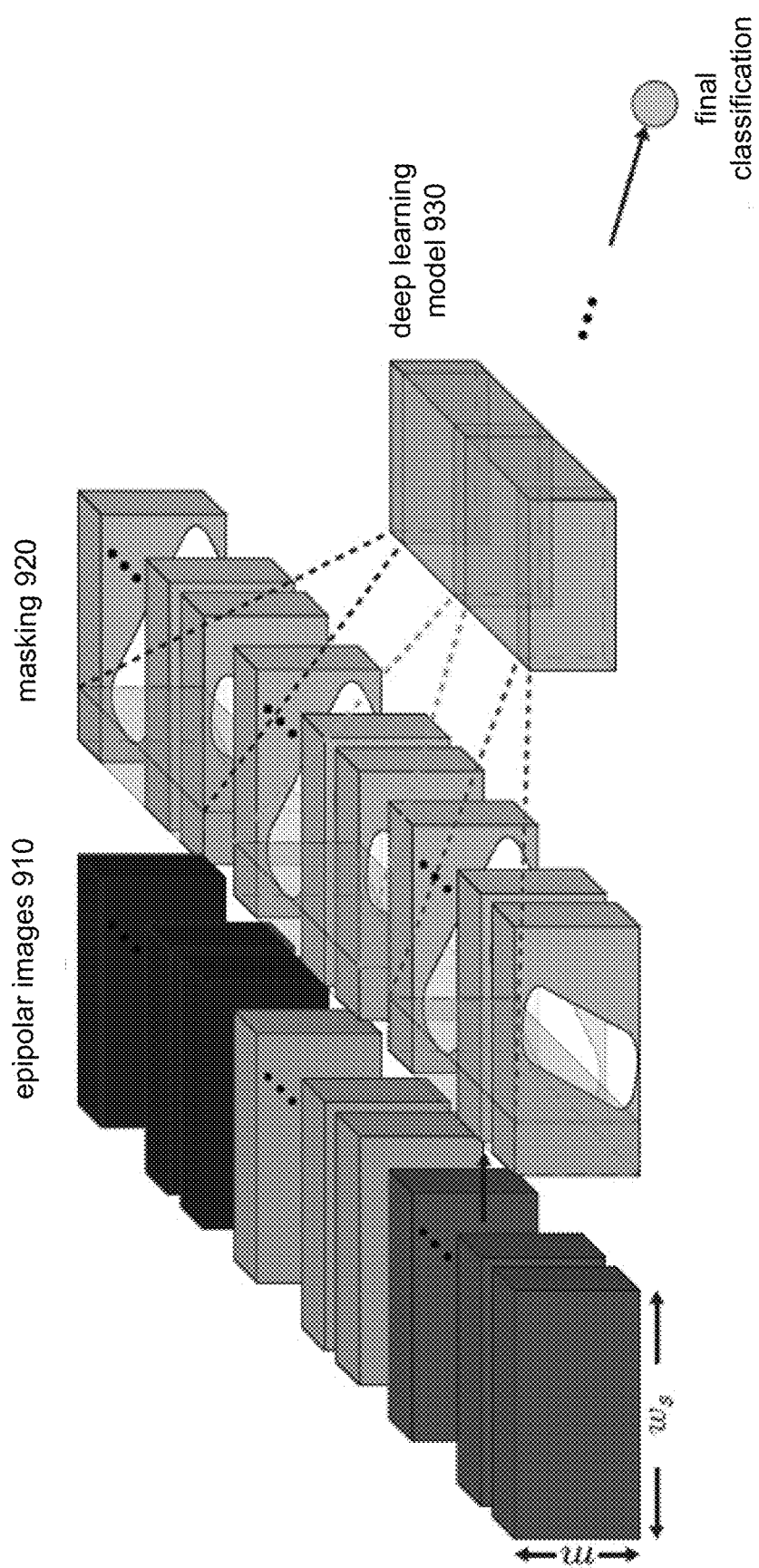

In the examples thus far, the masking is applied in the (image) domain. That is, an (x,y) mask is defined and applied to one of the views, which is a slice of the light-field data along an (x,y) plane. FIG. 9 provides an example where the masking is applied in a different domain. Here, the inputs are epipolar images. Epipolar images 910 are slices of the light-field data along the (x,u) plane—or some other plane that is a hybrid of (image) coordinates and (view) coordinates. In a specific example, the inputs are the horizontal and vertical epipolar images for each row or column of the input light-field image. The horizontal epipolar images are the slices $L^i(x, y=y_m, u, v=0)$ for m=1 ... $h_s$, and the vertical epipolar images are the slices $L^i(x=x_n, y, u=0, v)$ for n=1 ... $w_s$. These epipolar images 910 are then concatenated into a long cube, multiplied by their corresponding masks 920 and passed into the network 930 as shown in FIG. 9.

Notice also that the (channel) coordinate is re-ordered. All the red epipolar images are together, all the green ones are together and all the blue ones are together, suggesting that some reduction along the (channel) dimension is achieved by the deep learning model.

Figure 10:
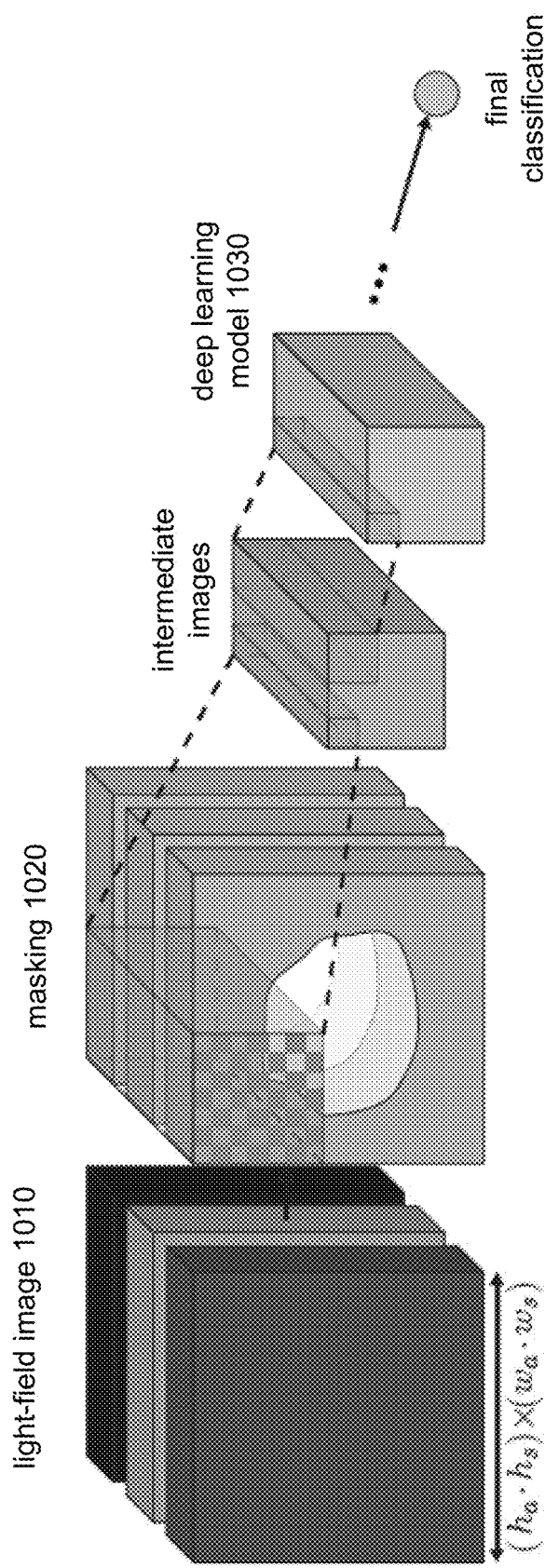

In FIG. 10, the masking 1020 is applied to data that is close to the full light-field images 1010. Then a filter for the (view) dimension of size $h_a \times w_a$ with stride $h_a, w_a$ is applied. The stride is the amount by which the filter shifts.

One channel is output in the intermediate image (as seen in FIG. 10). After passing this layer, the image reduces to the same spatial size as the original 2D input. Specifically, let this layer be termed I (intermediate), then the output of this layer for each spatial coordinate (x,y) and channel j is $$I^j(x, y) = g\left(\sum_{i=r,g,b} \sum_{u,v} w_i^j(u, v) L^i(x, y, u, v)\right) \forall j = 1, ..., C, \quad (1)$$

where L is the input (RGB) light-field image, i is the index for the color channel of the input image (i takes the values red, green and blue), j is the index for channels in layers after the input layer, w(u,v) are the weights of the (view) filter, and g is the rectified linear unit. As seen from the formula, the weights w of a channel j combine different color channels i. The output given by Eqn. 1 is passed into the remaining part of the deep learning architecture 1030.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

Alternate embodiments are implemented in computer hardware, firmware, software, and/or combinations thereof. Implementations can be implemented in a computer program product tangibly embodied in a machine-readable storage device for execution by a programmable processor; and method steps can be performed by a programmable processor executing a program of instructions to perform functions by operating on input data and generating output. Embodiments can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

What is claimed is:

1. A method implemented on a computer system comprising a processor, the processor executing instructions to effect a method for classifying an object, the method comprising:
   receiving a light-field image of the object, the light-field image comprising a plurality of views of the object taken simultaneously from different viewpoints;
   pre-processing the light-field image to produce derivative image data, the pre-processing comprising:
      determining masking to select regions of interest within the light-field image, and
      applying the masking; and
   applying the derivative image data as input to a deep learning model, the deep learning model producing a decision classifying the object, wherein producing the decision classifying the object comprises:
      the deep learning model producing a plurality of intermediate decisions classifying the object; and
      applying a voting schema to the intermediate decisions to produce the decision classifying the object.

2. The method of claim 1 wherein determining masking comprises:
   extracting depth information for the object from the plurality of views; and
   determining the masking based on the extracted depth information.

3. The method of claim 1 wherein applying masking consists of:
   applying masking to only one of the views, wherein the derivative image data is not based on any other of the views.

4. The method of claim 1 wherein applying masking comprises:
   applying masking to each of the plurality of views.

5. The method of claim 4 wherein:
   determining masking comprises determining separately for each of the plurality of views, the masking to be applied to that view; and
   applying masking comprises, for each of the views, applying the masking for that view.

6. The method of claim 1 wherein:
   pre-processing the light-field image comprises producing epipolar images from light-field data in the light-field image; and
   applying masking comprises applying masking to the epipolar images.

7. The method of claim 1 wherein applying masking comprises:
   applying masking directly to the light-field image.

8. The method of claim 1 wherein:
   pre-processing the light-field image comprises reducing light-field data in the light-field image with respect to image, view and/or channel dimensions; and
   applying masking comprises applying masking to the reduced light-field data.

9. The method of claim 1 wherein the light-field image comprises different color channels, and applying masking comprises applying masking separately to each of the color channels.

10. The method of claim 1 wherein the masking is binary.

11. The method of claim 1 wherein the masking is continuous.

12. The method of claim 1 wherein the voting schema weights the intermediate decisions, and the weight for each intermediate decision is related to the masking applied to produce that intermediate decision.

13. The method of claim 1 wherein the voting schema uses a machine learning model to produce the decision classifying the object.

14. The method of claim 1 wherein the object is an eardrum of a patient, and the decision is a decision classifying a condition of the eardrum.

15. The method of claim 1 wherein the deep learning model comprises a plurality of layers, each layer including a set of filters applied to a set of inputs for the layer, and a non-linear function applied to an output of the filtering.

16. A method implemented on a computer system comprising a processor, the processor executing instructions to effect a method for classifying an object, the method comprising:
   receiving a light-field image of the object, the light-field image comprising a plurality of views of the object taken simultaneously from different viewpoints;
   pre-processing the light-field image to produce derivative image data, the pre-processing comprising:
      determining masking to select regions of interest within the light-field image, wherein determining masking comprises determining masking based on image intensity of light-field data in the light-field image; and
      applying the masking; and
   applying the derivative image data as input to a deep learning model, the deep learning model producing a decision classifying the object.

17. A method implemented on a computer system comprising a processor, the processor executing instructions to effect a method for classifying an object, the method comprising:
   receiving a light-field image of the object, the light-field image comprising a plurality of views of the object taken simultaneously from different viewpoints;
   pre-processing the light-field image to produce derivative image data, the pre-processing comprising:
      determining masking to select regions of interest within the light-field image, wherein determining masking comprises using a machine learning model to determine the masking; and
      applying the masking; and
   applying the derivative image data as input to a deep learning model, the deep learning model producing a decision classifying the object.

* * * * *